United States Patent [19]

Rembaum et al.

[11] Patent Number: 4,929,400
[45] Date of Patent: May 29, 1990

[54] PRODUCTION OF MONODISPERSE, POLYMERIC MICROSPHERES

[75] Inventors: Alan Rembaum; Won-Kyu Rhim, both of Pasadena; Michael T. Hyson, Glendale; Manchium Chang, Los Angeles, all of Calif.

[73] Assignee: California Institute of Technology, Pasadena, Calif.

[21] Appl. No.: 856,201

[22] Filed: Apr. 28, 1986

[51] Int. Cl.⁵ .............................................. B28B 9/10
[52] U.S. Cl. ........................................ 264/10; 264/5; 264/9; 264/13
[58] Field of Search ...................... 264/15, 10, 5, 9, 24, 264/23, 13, 236, 345

[56] References Cited

U.S. PATENT DOCUMENTS

| | | | |
|---|---|---|---|
| 4,267,234 | 5/1981 | Rembaum | 428/403 |
| 4,267,235 | 5/1981 | Rembaum et al. | 428/407 |
| 4,339,337 | 7/1982 | Tricot et al. | 252/62.54 |
| 4,438,239 | 3/1984 | Rembaum et al. | 525/54.1 |
| 4,553,917 | 11/1985 | Lee | 425/6 |
| 4,623,706 | 11/1986 | Timm et al. | 526/88 |

*Primary Examiner*—Jan H. Silbaugh
*Assistant Examiner*—Mary Lynn Fertig
*Attorney, Agent, or Firm*—Marvin E. Jacobs

[57] ABSTRACT

Very small, individual polymeric microspheres with very precise size and a wide variation in monomer type and properties are produced by deploying a precisely formed liquid monomer droplet, suitably an acrylic compound such as hydroxyethyl methacrylate into a containerless environment. The droplet which assumes a spheroid shape is subjected to polymerizing radiation such as ultraviolet or gamma radiation as it travels through the environment. Polymeric microspheres having precise diameters varying no more than plus or minus 5 percent from an average size are recovered. Many types of fillers including magnetic fillers may be dispersed in the liquid droplet.

14 Claims, 1 Drawing Sheet

PRODUCTION OF MONODISPERSE, POLYMERIC MICROSPHERES

ORIGIN OF THE INVENTION

The invention described herein was made in the performance of work under a NASA contract, and is subject to the provisions of Public Law 96-517 (35 USC 202) in which the contractor has elected to retain title.

TECHNICAL FIELD

The present invention relates to a process for the production of polymeric particles and, more particularly, this invention relates to a process for the production of evenly-sized, magnetic or non-magnetic, microspheres by the polymerization of falling or suspended uniformly-sized and shaped droplets in a containerless environment.

BACKGROUND OF THE INVENTION

There are extensive biological, medical and industrial uses for small polymeric particles having uniform size and even more extensive uses for magnetic polymeric microspheres. Small polymeric microspheres, especially those containing covalent binding functional groups, are finding increasing uses in separation processes such as affinity chromatography, in labelling and sorting of biological cells, in diagnostic testing and in clinical treatment. Metal and metal oxide containing microspheres, particularly those containing magnetically susceptible materials, find use in catalysis, and electron microscopy. Uniformly-sized particles can be utilized to calibrate instruments or filters and the like.

Magnetic particles also find use in biology as substrates or carriers for enzymes or proteins and in cell biology as substrates derivatized with ligands capable of labelling specific cells. The labelled cells can then be separated from a mixture containing both labelled and unlabelled cells or from mixtures of labelled cells with other proteinaceous material. Magnetic microspheres can also be utilized to deliver a pharmaceutical to a specified location or organ in an animal or person.

Microspheres containing magnetic oxides and/or electron dense metals such as iron can also be useful in cell identification by electron microscopy. Rembaum, et al (*Science*, 208: 364, 368, [1980]) disclose identification of malignant cells in mixture with normal cells by this technique. U.S. Pat. No. 4,169,804 discloses use of magnetic-ligand particles for measurement of hormones and vitamins. Magnetic microspheres labelled with specific antibodies have also been utilized to specifically bind to malignant cells in the treatment of leukemia.

Magnetic polymeric microspheres have been used, for example, to remove cancerous cells from bone marrow as a treatment for neuroblastoma. The antibody-containing microspheres were mixed with both normal and cancerous bone marrow cells. The antibodies attached the microspheres only to the cancerous cells. The microsphere-cell conjugates were then removed from the solution by being attracted to a strong magnet placed adjacent the wall of the container. The cleaned marrow cells were then reimplanted in the patient. To date, 55 patients, many of them children, have been treated by this technique with promising results (Treleaves et al, Lancet, pp. 70-73, Jan. 14, 1984). Molday, et al., (Nature, 268: 437-438 [1974]) and U.S. Pat. Nos. 4,157,323; 4,177,253; and 4,267,235 also disclose use of magnetic microspheres in the labelling and separation of specific animal cells.

DESCRIPTION OF THE PRIOR ART

Magnetic polymers have been formed by dispersing the magnetic powders in preformed polymers. This technique is limited to soluble or meltable polymers and requires separate post-polymerization apparatus and processing and adds an additional energy cost to the product. Magnetic polymeric materials are generally produced by suspending magnetic particles in the liquid phase of the polymerizable formulation and polymerizing the monomers in presence of the magnetic particles to form polymeric microspheres. Polymerization can be by addition or condensation and can be conducted in bulk, emulsion, suspension or solution. Many of the magnetic particles are not incorporated into the resulting polymer and the size of the polymer particles must necessarily be larger than the magnetic particles. It is difficult to maintain a uniform suspension of the magnetic particles. The polymer particles are not evenly sized and do not contain a uniform amount of magnetic particles. The excess magnetic particles must be recovered from the polymerization formulation in post-polymerization processing steps.

U.S. Pat. No. 4,339,337 discloses the preparation of magnetic beads by dispersing a magnetic filler in a solution of polymer dissolved in a polymerizable vinyl aromatic compound and polymerizing the compound. In U.S. Pat. No. 4,358,388, the magnetic filler is dispersed in an organic phase containing dissolved initiator and vinyl aromatic monomer. The organic phase is emulsified and polymerized to form a latex.

Magnetic polyglutaraldehyde microspheres are prepared by polymerization of glutaraldehyde in presence of magnetic particles (U.S. Pat. Nos. 4,267,234 and 4,267,235) and magnetic polyacrolein microspheres are also prepared by in-situ polymerization of acrolein in presence of magnetic particles (U.S. Pat. No. 4,438,239).

U.S. Pat. No. 4,234,496 discloses the formation of magnetic polyvinyl pyridine beads by complexing the amine group with metal salts and reducing the complex to form finely divided free metal or metal oxides. This technique is limited to complexing with certain acids and the glass transition temperature of polyvinyl pyridine is low.

Porous polystyrene particles containing magnetic iron oxide have been prepared by impregnating porous nitrated polystyrene particles with an iron salt such as ferrous chloride, ferric chloride or their mixture. Magnetic polymer particles having much higher magnetic strength are produced by the method described in co-pending application, Ser. No. 786,649, filed Oct. 11, 1985. The method utilizes a $NO_2$ containing polymer substrate. Magnetic oxide is introduced into the polymer substrate by reacting metal and the polymer in the presence of mineral acid. Very fine, black, magnetic oxide is deposited on the surface of the polymer.

Uniformly sized, small microspheres of the order of 100 Angstroms to 10 microns in diameter are preferred as carriers for biological substances such as antigens or antibodies. Uniformly-sized, small microspheres provide monodispersity and result in less non-specific binding to the surface of the cells or to the surface of containers.

Most of the prior methods are incapable of producing uniformly sized or shaped spherical particles. The particles are somewhat ovoid in shape and are produced in a range of sizes. The magnetic oxide content also varies considerably. In some methods the magnetic oxide is present only on the surface of the polymeric particles.

A few types of monodisperse, polymeric particles can be produced by current techniques. The particles that are available are very expensive. Some very uniform particles produced in space by Vanderhoff are being sold by the U.S. Bureau of Standards for $500,000 per gram. Monodisperse polymer particles can not be produced from most types of monomers by the methods presently utilized.

Only a complicated process, stepwise seed growth emulsion polymerization, produces large, polymer microspheres of nearly uniform size above 2 microns. This method is very lengthy, leaves unwanted impurities in the final product and can only be used with a few materials or monomers—all of which are hydrophobic. The microspheres must be washed and freeze-dried to obtain a dry product. The microspheres can be coated with magnetite to make them magnetic. However, the magnetite forms a loose surface coating which interferes with the attachment of antibodies. The magnetite contents per microsphere is limited to about 30% since the magnetite is present as a surface coating. The densities of polymeric particles produced in the presence of fillers such as dense metals or metal oxides such as ferrite is very limited. As the concentration of metal or metal oxide filler increases the polymeric particles fall out of the emulsion suspension and clump together. Hydrophilic, monodisperse particles can not be produced by current methods and metal containing hydrophilic, monodisperse particles have never been produced by any method.

STATEMENT OF THE INVENTION

Very small, individual polymeric microspheres with very precise size and a wide variety of properties can be produced in accordance with the present invention. Very pure, monodisperse particles can be produced from a wide variety of monomers, including hydrophilic monomers, as well as many substances which can be sprayed in a liquid form, such as polymers, proteins, waxes, starches and even glasses and metals. The particles can be produced in a wide range of particle sizes, densities and morphologies. Many types of fillers can be incorporated into the particles, e.g., magnetic fillers such as magnetite. The fillers are distributed in the volume of the particles rather than on the surface as provided by some of the prior methods of producing magnetic, polymeric particles. The microsphere particles can contain covalent functional groups on the surface capable of further reaction with and attachment to other materials such as fluorescent dyes, antibodies or other proteins. Macroreticular particles can also be made using the present invention simply by incorporation of a non-reactive diluent with the monomers.

The microspheres are produced in accordance with the invention in a simple, one-step process. A uniformly-sized droplet of polymerizable liquid is formed in an injector device. The droplet is injected into a containerless environment and assumes a spheroid shape as it falls or travels through the environment. The spheroid droplet is subjected to polymerizing inducing radiation as it falls through the environment. Polymeric microspheres, having precise size range with diameters varying no more than plus or minus 5 percent, usually plus or minus 1 percent from an average size, are recovered.

The method is applicable to any monomer that can be provided in liquid form. The monomer can be hydrophobic or hydrophilic. The bulk monomer can be a liquid at ambient temperature or can be dissolved in solvent. The monomer can also be a solid which is heated before and after being fed to the injector in order to convert the solid material to a liquid. Fillers can be predispersed in the liquid monomer to form a uniform dispersion before the liquid is formed into droplets. The process of the invention can be conducted without solvent, catalyst, suspending agents, emulsifiers or other reactants providing a very pure particle directly and avoiding costly post-polymerization purification techniques. Purity is further enhanced by the containerless environment in which the particle is exposed during polymerization to a gaseous, vacuum or near vacuum atmosphere containing very few molecules. The very pure environment prevents contamination by extraneous impurities that could be present in a liquid polymerization media or impurities provided by the container itself that can be carried into solution. The use of radiation induced polymerization also eliminates the introduction of impurities provided by residues of catalysts, initiators or suspending agents utilized in emulsion polymerization.

Fluid dynamic forces cause the liquid droplet to assume a spherical shape. Subjecting the liquid sphere to polymerizing radiation while spherical results in the freezing of the object in a spherical shape as it is converted to a solid. In contrast, the forces in a stirred, liquid emulsion tend to produce egg-shaped polymeric beads. Radiation-induced polymerization rapidly converts the liquid droplets into a solid sphere with the expenditure of little energy. The dry product is produced in a form ready for use.

The evenness of the size of the microspheres is due, in large part, to the injection of evenly sized drops into the polymerizing environment. A wide variety of sizes, including large sizes, can be produced since larger drops of higher density can readily be levitated while being polymerized. The levitation technique is not sensitive to the ionic or surface characteristics of the droplet and hydrophilic or hydrophobic monomers can readily be polymerized greatly increasing the range and type of materials available in monodisperse form. The internal dispersion of the magnetic or other filler reserves the functional sites on the surface. The surface is in a more biocompatible form and in a form more available for attachment to proteins, dyes or other subtrates.

The monodisperse polymeric microspheres produced in the method of the invention have many uses. The microspheres can be used in polymeric, magnetic separation of cancer cells or in labelling and visualization of cellular structures. The particles can be used for column packing material for liquid chromatography as well as for affinity chromatography. The uniformity of size and shape are major factors in the column efficiency obtained. The microsphere particles have high surface area and can be made porous, like sponges, a form in which they are useful as catalysts or catalyst supports The pure hydrophilic materials have a low, non-specific absorption of hydrophilic materials such as proteins. Their large, uniform size coupled with mechanical strength allows high flow rates and high pressures to be used without breaking the particles. Materials stable in strong acids and bases can be made, allowing their use in a wide range of conditions. Also, if a catalyst were carried on the surface of a magnetic particle, the catalyst particle could be magnetically recovered after the reaction was completed. Further, by adding various metals, such as platinum, the particles themselves could be rendered catalytic. The magnetic particles are electron dense and therefore could be used to visualize biological or other structures in an electron microscope without the necessity to coat the particle with gold. Instruments, filters and the like can be calibrated using the very uniform, particles produced in the invention. New forms of paint or metal coatings for data storage can be fabricated using microsphere particles produced by the invention. The microspheres will also find use in diagnosis, therapy and drug targeting.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
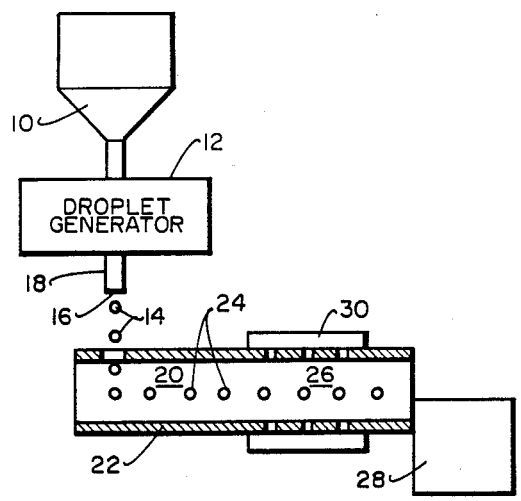
FIG. 1 is a schematic view of a general system for producing monodisperse, polymeric microspheres according to the invention.

The process of the invention involves the steps of (1) liquid droplet formation, (2) spheroidization of the droplet and (3) conversion of the droplet to a polymerized solid. Steps (2) and (3) are conducted in a containerless environment. Containerless environment of the invention means a process in which the droplet does not contact the walls of the container. Referring now to FIG. 1, a polymerizable liquid is fed from supply reservoir 10 to the droplet generator 12. A droplet 14 is deployed from outlet 16 of a nozzle 18 into a column 20 of gaseous environment contained within a container 22. As the droplet moves through the column 20, it is formed into a sphere 24 by fluid dynamic forces.

The droplet solidifies in the adjacent solidifying zone 26 and is collected in collector 28. The zone 26 can contain a jacket 30 of cryogenic liquid or it can contain a source of polymerizing radiation. If the droplet is frozen into spherical shape it can later be polymerized by applying radiation to the spherical particle.

The container is of a length sufficient to complete the solidification process. In the case of slowly polymerizing liquid droplets, completion of polymerization may require thirty minutes or more. This would require a very long drop chamber. It is therefore preferred to levitate the droplet during polymerization. Levitation may be provided by acoustic, aerodynamic or electrostatic forces. Electrostatic levitation is preferred since acoustic or aerodynamic forces are more likely to distort the shape of the liquid droplet. The levitation column can be horizontal or vertical. Horizontal columns can be slightly tilted so that the droplets and hardened particles are pulled toward the outlet of the device by the action of gravity.

Drop generators capable of developing evenly-sized drops are readily available commercially. One type of drop generator is based on Rayleigh instability of a charged fluid. A hollow needle is filled with liquid so that a partial drop protrudes from the end of the needle. Sufficient charge applied to the drop causes the drop to deform into a Taylor cone and to be ejected from the cone. Very small charged droplets of equal size are ejected from the apex of the cone. Control of the size of the tube, the character of the liquid and the amount of charge determines the drop size.

A piezoelectric drop generator could be used similar to those used in cell sorters and ink jet printers. A piezoelectric crystal connected to the back of a small fluid filled cavity having a small opening in front is energized with a voltage pulse. The piezoelectric crystal expands, reducing the cavity volume. A small, constant-size droplet is ejected with each pulse of the crystal. Drops can be made in a size ranging from 1000 Angstroms up to 100 microns.

Figure 2:
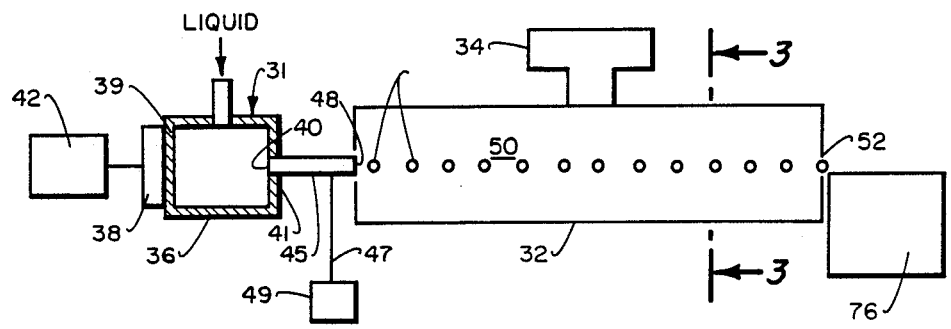
FIG. 2 is a view in elevation of a monodisperse microsphere producing apparatus.
Figure 3:
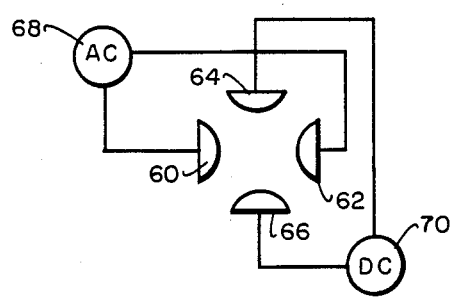
FIG. 3 is a view in section taken along line 3—3 of FIG. 2.

A system for continuously producing uniform microspheres is illustrated in FIGS. 2 and 3. The system includes a drop generator 31, a quadropole electrodynamic levitator 32 and a radiation source 34. Suitable drop generators are piezoelectric injectors or electrostatic drop ejectors. The drop generator 31 illustrated is similar to the injector used in ink jet printers or cell sorters. A cavity 36 has a piezoelectric crystal 38 mounted on the rear wall 39 and a small outlet 40 in the front wall 41. When the crystal 38 is pulsed by the power supply 42, the crystal expands, reducing the volume of the cavity 36 and ejecting a small, constant-size droplet 44 of polymerizable liquid through the nozzle 45 with each pulse. Drops can readily be made in a size range from 1000 Angstroms to 100 microns. The drop can be charged by applying a voltage to the tip of the nozzle 45 by means of a lead 47 connected to the high voltage terminal of a power supply 49. The droplet 44 is deployed into the inlet 48 of the central column 50 of the levitator 32. The drop assumes a spherical shape due to inherent fluid dynamic forces. The droplet 44 moves horizontally along the column by tilting the column toward outlet 52.

The spherical droplets 44 are deployed into the central column of the levitator 32 and become trapped in the field of the levitator. The levitator 32 can take the form of four opposed electrodes 60, 62, 64, 66. An A.C. field is applied to the side electrodes 60, 62 from an A.C. source 68 while a D.C. field is applied to the top and bottom electrodes 64, 66 from a source 70. The varying electric field produces a centering force toward the longitudinal axis while the D.C. field serves to cancel the effect of gravity. The D.C. field would not be needed in a microgravity environment such as space. Since the forces that can be imparted to the particles by electrostatic levitators is limited, the zero-gravity of space will permit the positioning and control of large numbers of particles of high densities. This may provide an effective mass production environment.

Many drops can be held at one time in a row along the axis of the levitator. Liquid drops of up to 1 mm can be supported in 1 g gravity for several hours. Therefore, the smaller polymer particles can easily be held. The tubes of the levitator need not be continuous but can be arranged in segments, each controlled separately. This allows the drops to be moved along the levitator in steps, or moved to a different level and turned around corners and the like which will facilitate large volume production of the microspheres.

Once held in the levitator, the droplets will be polymerized by applying a beam of radiation such as ultraviolet energy from a radiation source 34 such as a high pressure mercury lamp or a UV laser. After polymerization, the charged drops will be released from the levitator and collected as a dry product in a container 76 by attraction by a grounded plate, an electromagnet or permanent magnet placed on the wall of the container 76. The entire system can readily be automated to allow continuous production of the microspheres using the levitation system much like a factory conveyor belt. The environment of space also provides a vacuum environment for the column. Inert atmospheres such as vacuum, nitrogen or argon can be provided on land based systems by enclosing the column from the injector inlet to the particle outlet. The like-charged beads repel each other maintaining separation along the axis of the column.

The liquid droplets may be neat, i.e., pure monomer, or may contain vaporizable solvent or diluent such as water or organic solvent usually from 0.1 to 30 percent by weight of solvent or diluent. The monomer is polymerizable by the radiation applied to the column, either directly or indirectly by means of a photoinitiator that is activated by the radiation to generate a polymerizing species such as a free radical. Suitable U.V. photoinitiators such as a benzoin alkyl ether may be present in an amount of 0.1 to 10 percent. The polymerization reaction occurs at higher rates as the amount of photoinitiator is increased.

The droplets may also contain a dispersion of small filler particles such as 0.1 to 60 percent by weight of dense metals or metal oxides. Fluorescent and nonfluorescent dye may also be incorporated with the mixture to prepare colored particles.

The magnetic particles may be blended into the polymerizable liquid from a suspension of the magnetic particles in water or organic liquid. Magnetite suspended in an aqueous liquid containing a surfactant suspending agent is commercially available. Aqueous suspensions of magnetite without surfactants can be made. Other fillers that can be utilized are colloidal iron, cobalt or nickel which are all strongly magnetic. High intensity magnetic fields can be obtained by dispersing samarium-cobalt or neodymium-cobalt magnetic materials in the polymerizable liquid.

Unsaturated compounds, particularly acrylic monomers, polymerize by addition polymerization when subjected to thermal, U.V., gamma or other actinic radiation. Representative hydrophobic acrylic monomers are the acrylate esters such as compounds of the formula:

where $R^1$ is hydrogen or lower alkyl of 1-8 carbon atoms, $R^2$ is alkylene of 1 to 12 carbon atoms and X is a hydrophobic group such as lower alkyl or alkoxy of 1 to 8 carbon atoms. Representative acrylate esters are methyl methacrylate, methyl acrylate, ethyl methacrylate or propyl methacrylate.

Hydrophilic and functional microspheres provide biocompatible substrates having surface sites available for covalent bonding. Hydrophilic surface also reduces the non-specific binding of protein on their surface which can cause the denaturing of protein and/or cross reactions. These monomers may be mono-unsaturated compounds containing a functional group such as aldehyde substituted acrylic monomers. Representative monomers are acrolein, acrylamide, methacrylamide, acrylic acid, methacrylic acid, dimethylamino-methacrylate or hydroxy-lower alkyl or amino-lower alkyl acrylates of the formula:

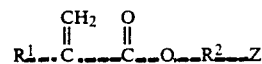

where $R^1$ is hydrogen or lower alkyl of 1-8 carbon atoms, $R^2$ is alkylene of 1-12 carbon atoms, and Z is —OH or $R^3$ or $R^4$ are individually selected from H, lower alkyl, or lower alkoxy of 1-8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Inclusion of polyunsaturated compounds also provides cross-linked beads which are less likely to agglomerate. The polyunsaturated compounds are generally present in the monomer mixture in an amount from 0.1 to 20 percent by weight, generally 6 to 12 percent by weight and are suitably a compatible diene or triene polyvinyl compound capable of addition polymerization with the covalent bonding monomer such as ethylene glycol dimethacrylate, trimethylol-propane-trimethacrylate, N,N'-methylene-bis-acrylamide (BAM), hexahydro-1,3,5-triacryloyl-s-triazene or divinyl benzene.

The monomer mixture may contain a large pecentage, suitably from 40 to 70 percent of sparingly water-soluble monomers having hydrophobic characteristics. The crosslinking agent is sometimes sparingly water soluble. Hydrophobic characteristics can also be provided with monomers such as lower alkyl acrylates, suitably methyl methacrylate or ethyl methacrylate or styrene, or a vinyl pyridine. Vinyl pyridines suitable for use in the invention are 2-vinyl pyridine, 4-vinyl pyridine and 2-methyl-5-vinyl pyridine.

The metal or metal compound particles are preferably fine, evenly-sized materials having a uniform diameter smaller than the resultant microsphere diameter, typically below 1000 Angstroms. The metals are preferably the electron dense heavy metals having a high atomic number above 50, preferably above 75 such as Pb, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard ceramic-type ferrites, such as lithium ferrites can also be used.

EXAMPLES OF PRACTICE FOLLOW

Microspheres were produced in the system of FIGS. 2 and 3. A liquid monomer composition was placed in the cavity of the injector. The levitator was operated with a A.C. field of some 4000 volts on the two side electrodes and a D.C. field of 500 volts applied to the top and bottom electrodes. The charged nozzle sprayer crystal was pulsed to produce droplets from 1000 Angstroms to 100 microns. In each case, the levitated droplets were irradiated with a UV light source for 20 minutes and the particles collected on a grounded plate. Sperical, polymeric, polyHEMA microspheres were collected.

EXAMPLE 1

The following composition was placed in the cavity of the injector:

| Material | Percent |
| --- | --- |
| Trimethylopropane triacrylate (TMPTA) | 5% |
| IRGACURE* 184 | 5% |
| Water | 10% |
| HEMA | 80% |

\* = 1-hydroxycyclohexyl phenyl ketone

Evenly sized, spheroid particles were produced.

EXAMPLE 2

| Material | Percent |
| --- | --- |
| TMPTA | 5% |
| IRGACURE | 5% |
| HEMA | 90% |

Evenly sized, spheroid particles were produced.

EXAMPLE 3

30 percent by weight of fine iron particles was added to the composition of FIG. 2 which was coated onto a slide as a layer. The layer polymerized when subjected to U.V. radiation.

It is to be realized that only preferred embodiments of the invention have been illustrated and that numerous substitutions, modifications and alterations are all permissible without departing from the spirit and scope of the invention as defined in the following claims.

We claim:

1. A method of forming uniformly sized, small, spherical, polymeric particles having a diameter from 100 Angstroms to 100 microns varying no more than plus or minus 5 percent from the average diameter without use of a catalyst comprising repeating the steps of:
    deploying a spheroidal droplet consisting essentially of a radiation polymerizable, unsaturated liquid monomer and absent catalyst or surfactant into a zone consisting of inert gas;
    levitating the droplet while in the zone;
    applying polymerization inducing radiation to the spherical droplet while in the zone and polymerizing the droplet throughout its volume to form a solid spherical particle; and
    recovering the solid particle.

2. A method according to claim 1 in which the zone is an elongated, horizontal zone having an inlet for receiving the droplet and an outlet for recovering the solid particle.

3. A method according to claim 2 in which the droplet is electrostatically levitated.

4. A method according to claim 3 in which the droplet is charged.

5. A method according to claim 1 in which the monomer is a hydrophilic acrylic compound.

6. A method according to claim 5 in which the acrylic compound contains a functional group selected from the group consisting of aldehyde, amine, carboxyl and hydroxyl.

7. A method according to claim 6 in which the compound is selected from the group consisting of compounds of the formula:

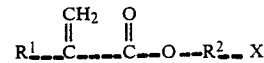

where $R^1$ is hydrogen or lower alkyl of 1 to 8 carbon atoms, $R^2$ is alkylene of 1 to 12 carbon atoms and X is a hydrophobic group selected from the group consisting of alkyl and alkoxy of 1 to 8 carbon atoms.

8. A method according to claim 7 in which the acrylic compound is hydroxymethylmethacrylate.

9. A method according to claim 1 in which the liquid droplet contains a dispersion of a solid material.

10. A method according to claim 9 in which the solid material is selected from the group consisting of metal and metal oxide.

11. A method according to claim 10 in which the solid material is magnetic attractable.

12. A method according to claim 1 in which the droplet contains 0.1 to 10% by weight of a radiation activatable free-radical generating photoinitiator.

13. A method according to claim 9 in which the liquid droplet contains from 0.1 to 60 percent by weight of dispersed solid material.

14. A method of forming uniformly-sized, spherical polymeric particles comprising repeating the steps of:
    deploying a spheroidal droplet consisting essentially of radiation-polymerizable, unsaturated liquid monomer into a zone containing inert gas;
    levitating the droplet while in the zone;
    solidifying the droplet into a solid, spheroid droplet while in the zone by lowering the temperature of the liquid droplet below its melting point; and
    then polymerizing the solid droplet by applying polymerizing inducing radiation to the solid droplet to form a polymerized solid particle.

* * * * *